(12) United States Patent
Wang et al.

(10) Patent No.: US 11,948,303 B2
(45) Date of Patent: Apr. 2, 2024

(54) METHOD AND APPARATUS FOR OBJECTIVE ASSESSMENT OF GASTROINTESTINAL CONDITIONS BASED ON IMAGES CAPTURED IN THE GI TRACT

(71) Applicant: CAPSOVISION, Inc., Saratoga, CA (US)

(72) Inventors: Kang-Huai Wang, Saratoga, CA (US); Chenyu Wu, Sunnyvale, CA (US); Gordon C. Wilson, San Francisco, CA (US)

(73) Assignee: CapsoVision Inc., Saratoga, CA (US)

( * ) Notice: Subject to any disclaimer, the term of this patent is extended or adjusted under 35 U.S.C. 154(b) by 292 days.

(21) Appl. No.: 17/352,291

(22) Filed: Jun. 19, 2021

(65) Prior Publication Data

US 2022/0277450 A1 Sep. 1, 2022

Related U.S. Application Data

(60) Provisional application No. 63/154,144, filed on Feb. 26, 2021.

(51) Int. Cl.
*G06T 7/00* (2017.01)
*A61B 1/04* (2006.01)
(Continued)

(52) U.S. Cl.
CPC ............ *G06T 7/0014* (2013.01); *A61B 1/041* (2013.01); *G06N 3/04* (2013.01); *G06T 3/40* (2013.01);
(Continued)

(58) Field of Classification Search
CPC ........... G06T 7/0014; G06T 3/40; G06T 5/50; G06T 7/55; G06T 7/62;
(Continued)

(56) References Cited

U.S. PATENT DOCUMENTS

| | | |
|---|---|---|
| 7,983,458 B2 | 7/2011 | Wang et al. |
| 2014/0348383 A1* | 11/2014 | Kamiya ................ G06V 40/10 382/103 |

(Continued)

FOREIGN PATENT DOCUMENTS

| | | |
|---|---|---|
| WO | WO 2020/191269 A1 | 9/2020 |
| WO | WO 2020/079696 A1 | 10/2020 |

OTHER PUBLICATIONS

"Automated and real-time validation of gastroesophageal varices under esophagogastroduodenoscopy using a deep convolutional neural network: a multicenter retrospective study (with video)", Gastrointestinal Endoscopy vol. 93, No. 2: 2021, pp. 424-432.e3.

*Primary Examiner* — Chan S Park
*Assistant Examiner* — Daniel C Chang
(74) *Attorney, Agent, or Firm* — Blairtech Solution LLC

(57) ABSTRACT

A method and apparatus of objective assessment of images captured from a human gastrointestinal (GI) tract are disclosed. According to this method, one or more images captured using an endoscope when the endoscope is inside the human gastrointestinal (GI) tract are received. Whether there is any specific target object is checked. When one or more specific target objects in the images are detected: areas of the specific target objects in the images are determined; an objective assessment score is derived based on the areas of the specific target objects in a substantial number of images from the images; where the step of detecting the specific target objects is performed using an artificial intelligence process.

26 Claims, 3 Drawing Sheets

(51) Int. Cl.
*G06N 3/04* (2023.01)
*G06T 3/40* (2006.01)
*G06T 5/50* (2006.01)
*G06T 7/55* (2017.01)
*G06T 7/62* (2017.01)

(52) U.S. Cl.
CPC .................. *G06T 5/50* (2013.01); *G06T 7/55* (2017.01); *G06T 7/62* (2017.01); *G06T 2207/10068* (2013.01); *G06T 2207/20084* (2013.01); *G06T 2207/20212* (2013.01); *G06T 2207/30092* (2013.01)

(58) Field of Classification Search
CPC . G06T 2207/10068; G06T 2207/20084; G06T 2207/20212; G06T 2207/30092; G06T 7/0012; A61B 1/041; A61B 1/000094; A61B 1/000096; G06N 3/04; G06N 3/0499; G06N 3/0464
See application file for complete search history.

(56) References Cited

U.S. PATENT DOCUMENTS

| | | | |
|---|---|---|---|
| 2016/0239706 A1 | 8/2016 | Dijkman et al. | |
| 2017/0161574 A1* | 6/2017 | Ick | G06V 20/52 |
| 2018/0153384 A1 | 6/2018 | Ikemoto et al. | |
| 2019/0110843 A1* | 4/2019 | Ummalaneni | A61B 34/30 |
| 2019/0304121 A1* | 10/2019 | Wang | G01B 11/00 |
| 2020/0113422 A1 | 4/2020 | Wang | |
| 2021/0034912 A1* | 2/2021 | Lisi | G16H 50/30 |
| 2021/0056322 A1* | 2/2021 | Hasegawa | B60W 30/16 |
| 2021/0345865 A1* | 11/2021 | Spillinger | G06T 7/0012 |

\* cited by examiner ately. In another
example, on-board data is transmitted electronically via
metal contacts disposed on the housing. For capsule images
either received through wireless transmission or retrieved
METHOD AND APPARATUS FOR OBJECTIVE ASSESSMENT OF GASTROINTESTINAL CONDITIONS BASED ON IMAGES CAPTURED IN THE GI TRACT

CROSS REFERENCE TO RELATED APPLICATIONS

The present invention is a non-provisional application of and claims priority to U.S. Provisional Patent Application Ser. No. 63/154,144, filed on Feb. 26, 2021. The U.S. Provisional Patent Application is hereby incorporated by reference in its entirety.

FIELD OF THE INVENTION

The present invention relates to process images captured by an endoscope in the gastrointestinal (GI) tract. In particular, the present invention discloses methods to derive a reliable objective assessment score for certain GI conditions.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiberoptic bundle. A conceptually similar instrument might capture an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot easily reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia.

An alternative in vivo image sensor that addresses many of these problems is the capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. This patent describes a capsule system using on-board storage such as semiconductor nonvolatile archival memory to store captured images. After the capsule passes from the body, it is retrieved. Capsule housing is opened and the images stored are transferred to a computer workstation for storage and analysis. The on-board data may also be retrieved through other means without the need for opening up the housing. For example, an optical transmitter along with an optical path through the housing can be used to retrieve the on-board data to an external optical receiver. In another example, on-board data is transmitted electronically via metal contacts disposed on the housing. For capsule images either received through wireless transmission or retrieved from on-board storage, the images will have to be displayed and examined by diagnostician to identify potential anomalies.

FIG. 1 illustrates an exemplary capsule system with on-board storage, where the capsule camera is in the human gastrointestinal (GI) tract 100. The capsule system 110 includes illuminating system 12 and a camera that includes optical system 14 and image sensor 16. A semiconductor nonvolatile archival memory 20 may be provided to allow the images to be stored and later retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. Processing module 22 may be used to provide processing required for the system such as image processing and video compression. The processing module may also provide needed system control such as to control the LEDs during image capture operation. The processing module may also be responsible for other functions such as managing image capture and coordinating image retrieval.

After the capsule camera traveled through the GI tract and exits from the body, the capsule camera is retrieved and the images stored in the archival memory are read out through the output port. The received images are usually transferred to a base station for processing and for a diagnostician to examine.

In order to obtain clear images, the digestive tract needs to be purged by drinking strong laxatives to clean out contents before imaging the digestive tract using endoscope (tethered or capsule). For capsule or tethered endoscope, the evaluation of bowel preparation cleanness based on captured images have been used. Such approach is very subjective that creates substantial inter-observer or even intra-observer variances. In practice, the most frequent used scales by the medical professionals consist of multiple categories as shown in Table 1.

TABLE 1

Bowel preparation cleanness categories.

| Cleanness category | Definition |
| --- | --- |
| Poor | The mucosa was largely obscured by opaque debris or turbid fluid. |
| Fair | A portion of the mucosa was obscured by turbid fluid and/or debris large enough to prevent reliable visualization of polyps > 5 mm in size |
| Good | The fluid was clear, and any small pieces of debris or mucus were dispersed across the image but generally separated enough to not obscure polyps > 5 mm in size. |
| Excellent | The fluid was clear, and the image was either free of debris or had only small bits of scattered debris. |

Besides the issue of subjective criteria in Table 1, it is very difficult for the doctors to remember the thousands or tens of thousands of images and to give an overall quantitative bowel preparation assessment accurately and reliably. The above assessment may also be applied to bowel disease severity score, such as Crohn's disease.

In the capsule or tethered endoscope procedure, only good and excellent bowel preparation are adequate bowel preparation and are considered acceptable. On the other hand, poor or fair cleanness needs to abort the procedure or redo the procedure. The large inter-observer and intra-observer variances often indicate erroneous diagnosis and require adequate bowel preparation to redo the procedure. This will result in waste of the resources. Furthermore, the same large variance may let the serious lesions undetected due to unacceptable bowel preparation.

The human observer based assessment of the bowel preparation condition not only is time consuming, but also is unreliable. Therefore, it is desirable to develop an automated method to objectively assess the bowel preparation condition based on imaged captured from the digestive tract. While the assessment of the bowel preparation condition is one task of interest, many other tasks currently performed by human observers are candidates for automated subjectively assessment according to the present invention. For example, assessment of certain diseases, such as Crohn disease, is desirable to be objectively and reliably.

BRIEF SUMMARY OF THE INVENTION

A method and apparatus of objective assessment of images captured from a human gastrointestinal (GI) tract are disclosed. According to this method, one or more images captured using an endoscope when the endoscope is inside the human gastrointestinal (GI) tract are received. Whether there is any specific target object is checked. When one or more specific target objects in the images are detected: areas of the specific target objects in the images are determined; an objective assessment score is derived based on the areas of the specific target objects in said one or more images; where the step of detecting the specific target objects is performed using an artificial intelligence process.

In one embodiment, individual scores for individual images in the images are determined respectively, where each individual score is determined based on the areas of the specific target objects in one individual image and image size of one individual image. Furthermore, the objective assessment score can be derived based on the individual scores. When there is no specific target object detected in one individual image, the areas of said one or more specific target objects in one individual image are treated as zero.

In one embodiment, the areas of the specific target objects in one or more images are scaled according to respective object distances of the specific target objects respectively in the images, where scaled areas of the specific target objects in the images are used for the step of deriving the objective assessment score. For example, the objective assessment score can be derived from a ratio of a first sum of the areas of the specific target objects, scaled according to object distances of the specific target objects, in the substantial number of images from the images and a second sum of entire areas of the substantial number of images from the images scaled by distance information within the substantial number of images respectively. In another embodiment, when one specific target object is away from a mucosa of the human gastrointestinal (GI) tract, the object distance of said one specific target object is derived from a first distance from a camera of the endoscope to the mucosa of the human gastrointestinal (GI) tract in a neighborhood area associated with said one specific target object In one embodiment, the objective assessment score is related to a sum of the areas of the specific target objects in the substantial number of images from the images.

In another embodiment, the objective assessment score corresponds to a sum of adjusted areas, by respective object distances, of the specific target objects in the substantial number of images from the images.

In yet another embodiment, the objective assessment score corresponds to a weighted sum of the areas of the specific target objects in the substantial number of images from the images. For example, weighting factors for the weighted sum of the areas of the specific target objects are dependent on conditions or characteristics of the specific target objects.

In one embodiment, the artificial intelligence process corresponds to a convolution neural network (CNN) process.

In one embodiment, the specific target objects comprise opaque debris and turbid fluid, and the objective assessment score is indicative of bowel preparation condition. In another embodiment, the specific target objects comprise inflamed organ tissues, erosion or ulcers in distal ileum and colon, and the objective assessment score is indicative of Crohn disease condition.

In one embodiment, at least a portion of the human gastrointestinal (GI) tract intended for examination is divided into multiple sections and the images associated with said at least a portion of the human gastrointestinal (GI) tract are divided into corresponding groups. Sectional scores are derived for corresponding sections and each sectional score is based on total areas of the specific target objects in the images in each respective section normalized by a number of images in each respective group. The objective assessment score is then derived from the sectional scores. For example, each sectional score can be derive based on a subset of images in each corresponding group in each corresponding section.

In one embodiment, a travelled distance by the endoscope in the human gastrointestinal (GI) tract is used to decide a normalization factor on the areas of the specific target objects in the substantial number of images from the images.

In one embodiment, bad images are identified and are excluded from the step of deriving the objective assessment score, where the bad images comprise over-exposed images and/or under exposed images and/or motion-smeared images.

In one embodiment, object distances of the specific target objects are used to aid identifying the specific target objects.

In one embodiment, the images are stitched to form one or more stitched images, and where the steps of detecting the specific target objects, determining the areas of the specific target objects and deriving the objective assessment score are performed based on the stitched images. In another embodiment, the steps of detecting the specific target objects, determining the areas of the specific target objects and deriving the objective assessment score are performed based on a subset of the images.

In one embodiment, individual images of the images are assigned grades according to the areas of the specific target objects and the grades are indicative of disease severity or bowel cleanness, where a number of images or a percentage of images with certain grades or a ranges of grades are used to determine the objective assessment score.

DETAILED DESCRIPTION OF THE INVENTION

Figure 1:
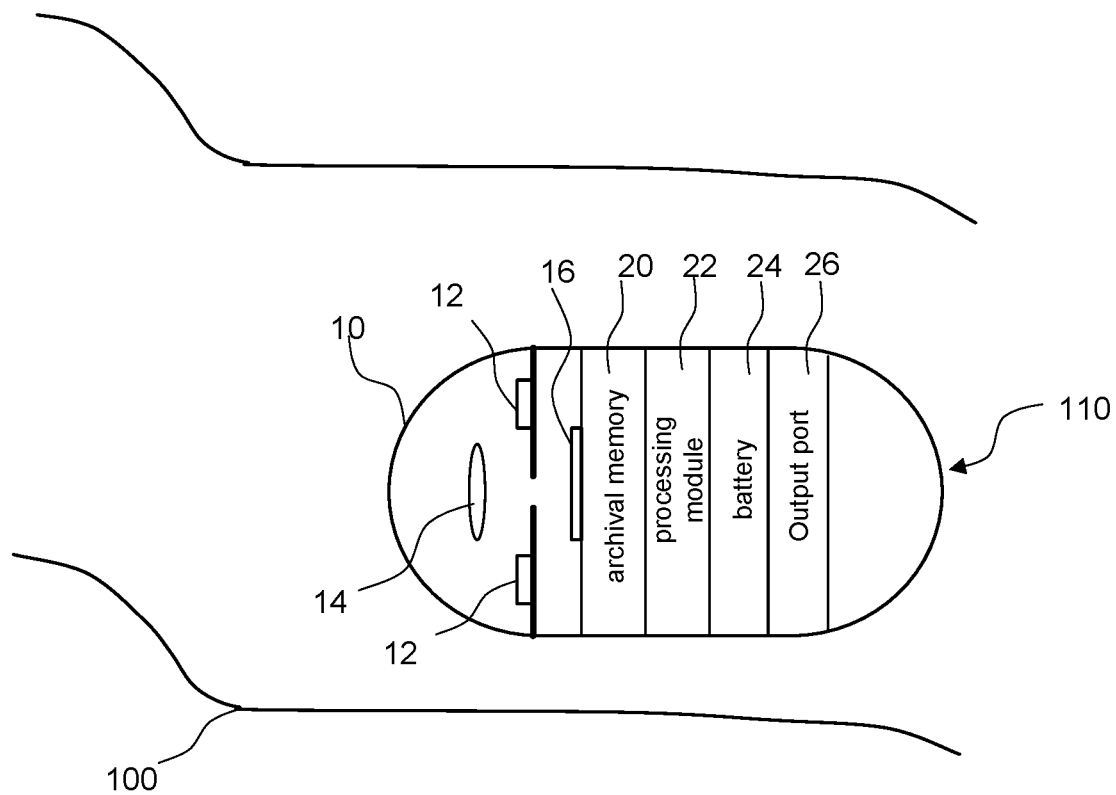
FIG. 1 illustrates an exemplary capsule system with on-board storage, where the capsule system includes illuminating system and a camera that includes optical system and image sensor.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. As mentioned before, endoscopes can be used for diagnosis of human gastrointestinal (GI) tract. The captured image sequence can be viewed to identify any possible anomaly. On the other hand, the capsule endoscope is administered by swallowing the capsule device through the mouth. The capsule device may be equipped with wireless transmitter to send captured images and/or other data to an external data receiver. Alternatively, on-board non-volatile memory can be used to record the captured images and/or other data. The conventional endoscope often refers to the tethered endoscope. In this disclosure, the endoscope may correspond to a tethered endoscope or a capsule endoscope. The term of "endoscope" and "tethered endoscope" may be used interchangeably when it is appropriate.

The images captured by the endoscopes or capsule cameras are usually used for diagnosis purposes to detect certain diseases of the digestive tract or to assess the conditions. The accuracy of the diagnosis or assessment heavily relies on the quality of the images. Among various factors affecting the image quality, bowel preparation cleanness plays a key role for image quality from the GI tract. If the bowel is not properly prepared for imaging, the images captured may be largely obscured by opaque debris or turbid fluid. If a doctor performs the diagnosis or assessment based on such images, reliable diagnosis or assessment cannot be achieved and the medical resources would be wasted. Therefore, acceptable bowel preparation becomes a prerequisite for reliable diagnosis or assessment of the GI tract. It is desirable to develop an automated system to qualify the captured images for further diagnosis or assessment before a medical professional spends time to examine the captured images.

While bowel preparation is important to provide an environment to obtain clear images of the GI tract, carefully controlling the endoscope during imaging to avoid or minimizing the possibility of missing any potential covered area is another important factor for endoscopy. A method and apparatus for detecting missed areas during endoscopy has been disclosed in U.S. Provisional Patent Application, Ser. No. 63/154,144, filed on Feb. 26, 2021. The U.S. Provisional Patent Application is hereby incorporated by reference in its entirety. According to this method, regular images captured by the camera are received while the endoscope travels through a human gastrointestinal (GI) tract. The regular images are mosaicked to determine any missed or insufficiently imaged area in a section of the human GI tract already travelled by the endoscope. If any missed or insufficiently imaged area is detected, information regarding any missed or insufficiently imaged area is provided. When a target area in the regular images is lack of parallax, the target area is determined as one missed area and an edge corresponding to a structure of the human lumen is highlighted. For a capsule endoscope, the endoscope can be configured to be controlled or steered to move so as to re-image the missed or insufficiently imaged area.

The present invention discloses automated diagnosis or assessment of bowel conditions based on captured GI images. According to the present invention, specific target objects are detected first. For example, the specific target objects may correspond to opaque debris, turbid fluid or bubbles for the assessment of bowel preparation condition. An image area associated with the opaque debris, turbid fluid or bubbles may have very different characteristics from the mucosa area. For example, an opaque debris often has dark greenish color while the mucosa has pink color. On the other hand, a bubble may have light gray color. When the specific target objects are specified, various methods can be used to automatically identify the specific target objects. Such methods may be based on image processing, computer vision or artificial intelligence.

In one embodiment, the areas of the specific target objects are used to derive objective assessment of a specific bowel condition. The area of a specific target object can be measured in the number of pixels, or physical size (e.g., square inches or square centimeters). In the example mentioned above, the specific bowel condition may correspond to various bowel conditions. Such as the bowel preparation condition. In one embodiment, the objective assessment is in a form of an objective score. For example, a score from 0 to 1 can be derived, where 1 indicates the worst condition of bowel preparation and 0 indicates perfect bowel preparation. In another embodiment, a higher objective assessment score may indicate better bowel preparation condition and a lower objective assessment score indicates worse bowel preparation condition. Other score ranges, such as 0 to 5, 10 or 100, may also be used. In one embodiment, the objective score can be mapped to the conventional categories of bowel preparation conditions in Table 1. In another embodiment, a threshold can be set and the bowel preparation is acceptable if the objective assessment score is below the threshold.

The specific target objects may correspond to the opaque debris, turbid fluid or bubbles for the case of objective assessment of a specific bowel condition. Therefore, smaller areas of the specific target objects imply better bowel preparation. However, instead of checking the state of the opaque debris, turbid fluid or bubbles, the method may alternatively check the state of image regions free from or substantially free from the opaque debris, turbid fluid. In this case, the specific target objects become regions free from the opaque debris, turbid fluid or bubbles or regions with very minor such quality defect. Therefore, larger areas of the specific target objects imply better bowel preparation in this case.

Figure 2A:
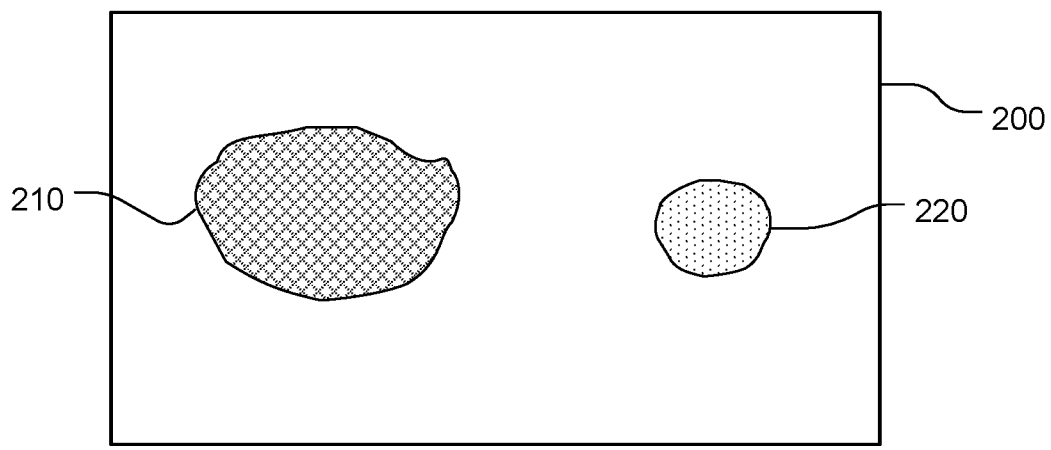
FIG. 2A illustrates an example of automated assessment of bowel conditions based on areas of the specific target object, where two specific target objects 210 and 220 are detected.

FIG. 2A illustrates an example of objective assessment of bowel conditions based on areas of the specific target objects. In image frame 200, two specific target objects 210 and 220 are detected. If the assessment task corresponds to determining the bowel preparation condition, the specific target objects may correspond to debris, bubble, or dark matter. In the example of FIG. 2A, object 210 may correspond to a dark matter and object 220 may correspond to a bubble. The areas of objects 210 and 220 can be automatically calculated using various known techniques in the field of image processing and/or computer vision. In one embodiment, a boundary box such as a rectangle or a polygon or other geometry shapes enclosing the object can be determined and the area of the boundary box can be calculated and can be used as an approximation of the area of the object. Furthermore, the assessment of specific target objects can be derived based on the areas of specific target objects.

In one embodiment, the objective assessment score is derived based on the areas of the specific target objects. The objective assessment score can be derived based on the sum of the areas of the specific target objects. Furthermore, the objective assessment score is derived from a substantial number of images from the captured images. In other words, not every image is used for deriving the objective assessment score. In another embodiment, the assessment score is determined as a ratio of the sum of areas of specific target objects and the area of image. In another embodiment, the substantial number is used to decide a normalization factor for the sum of the areas of said one or more specific target objects. In yet another embodiment, the objective assessment score corresponds to a weighted sum of the areas of the specific target objects in the images. The weighting factors for the weighted sum of the areas of the specific target objects can be dependent on conditions, characteristics or seriousness/severity of the specific target objects. For example, a larger weighting factor can be assigned to a specific target object corresponding to a disease area with a more severe condition (for disease condition assessment) or corresponding to a very dark debris (for bowel preparation cleanness assessment).

Figure 2B:
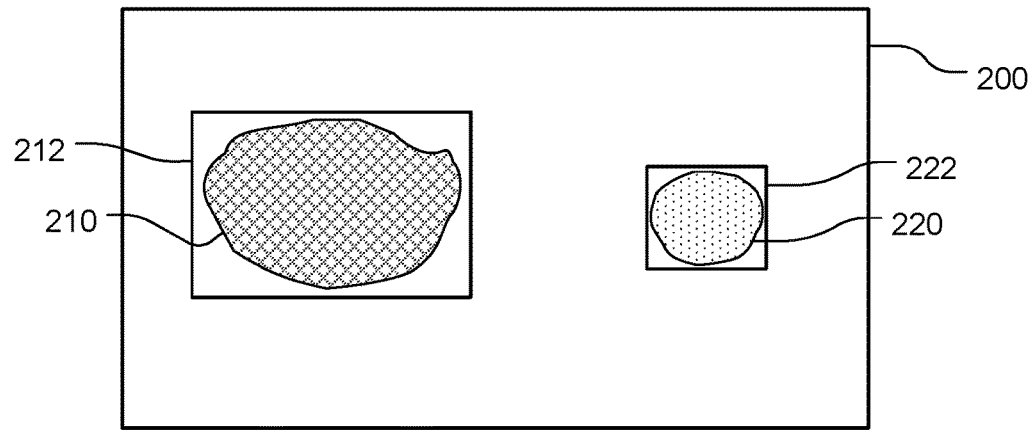
FIG. 2B illustrates an example of rectangular boundary boxes for the specific target objects in FIG. 2A.

FIG. 2B illustrates an example of rectangular boundary boxes (or bounding boxes) for the specific target objects in FIG. 2A. Again, the bounding boxes can be determined automatically using known image processing or computer vision techniques. The area of the rectangle or polygon can be readily calculated. In FIG. 2B, the specific target objects correspond to the opaque debris, turbid fluid for the case of objective assessment of bowel preparation state.

Artificial intelligence (AI) has been applied in the field of computer vision for decades. Various computer vision tasks such as object recognition, detection and classification can be effectively achieved using AI techniques. Among other machine learning algorithms, neural network is a computational model that is inspired by the way biological neural networks in the human brain process information. A convolutional neural network (CNN) is a class of neural network. Compared to the conventional fully connected neural network, CNNs take advantage of the hierarchical pattern in data and assemble patterns of increasing complexity using smaller and simpler patterns embossed in their filters. Therefore, on a scale of connectivity and complexity, CNNs are on the lower extreme and they can go deeper with more layers. By using a large number of NN layers, the CNN is capable of solving complicated tasks. In light of capability of CNNs, various dedicated hardware and software for implementing neural networks have been developed.

Figure 3:
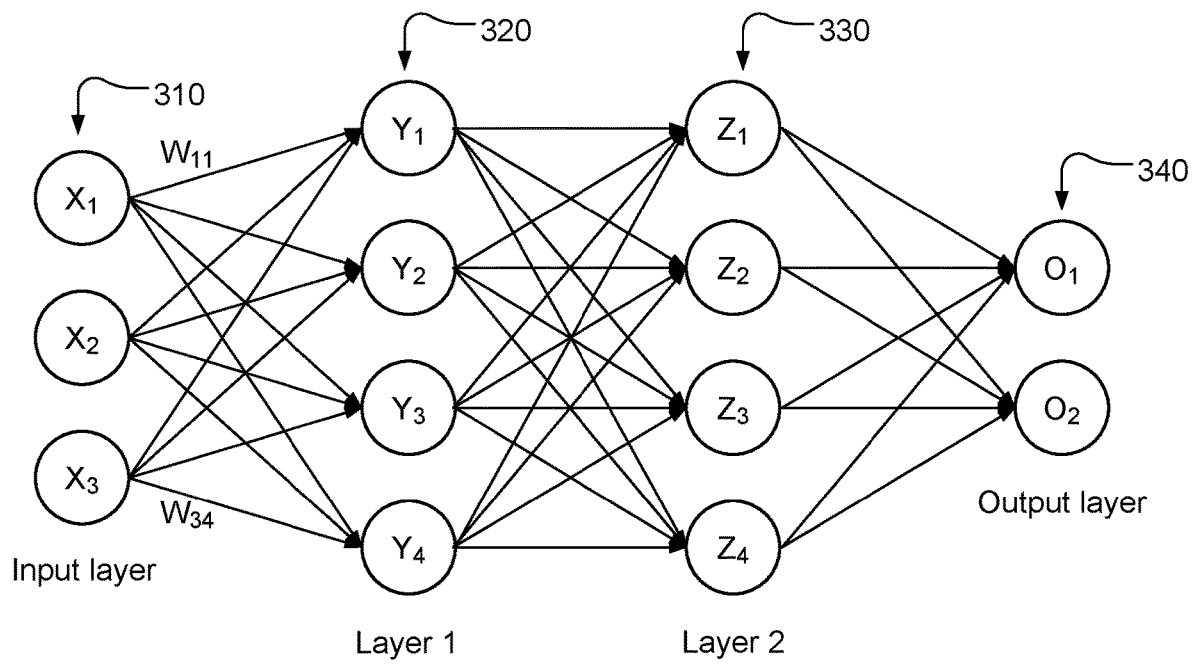
FIG. 3 illustrates an example of a simple neural network model with four layers, named as input layer 310, hidden layers 320 and 330, and output layer 340, of interconnected neurons.

FIG. 3 illustrates an example of a simple feedforward neural network with four layers, named as input layer 310, hidden layers 320 and 330, and output layer 340, of interconnected neurons. The output of each neuron is a function of the weighted sum of its inputs. A vector of values ($X_1 \ldots X_{M1}$) is applied as input to each neuron in the input layer. Each input in the input layer may contribute a value to each of the neurons in the hidden layer with a weighting factor or weight ($W_{ij}$). The resulting weighted values are summed together to form a weighted sum, which is used as an input to a transfer or activation function, $f_{act}(\bullet)$ for a corresponding neuron in the hidden layer. Accordingly, the weighted sum, $Y_j$ for each neuron in the first hidden lay can be represented as:

$$Y_j = \Sigma_{i=1}^{3} W_{ij} X_i, \quad (1)$$

where $W_{ij}$ is the weight associated with $X_i$ and $Y_j$. In general, the total number of input signals may be M1, where M1 is an integer greater than 1. There may be N1 neurons in the hidden layer. The output, $y_i$ at the first hidden layer becomes:

$$Y_j = f_{act}(\Sigma_{i=1}^{3} W_{ij} X_i + b_j), \quad (2)$$

where $b_j$ is the bias.

The output of each neuron may become multiple inputs for the next-stage neural network. Activation function of a node defines the output of that node given an input or set of inputs. The activation function decides whether a neuron should be activated or not. Various activation functions have been widely used in the field, which can be classified as a linear type and a nonlinear type. Nonlinear-type activation functions are widely used in the field.

For each neuron, $Z_j$ in the second hidden lay, $Z_j$ can be calculated similar to eqn. (1) with $Y_i$ as inputs and a different set of weighting factors $W'_{ij}$.

The output values $O_j$ can be calculated similarly by using $Z_i$ as input. Again, there is a weight associated with each contribution from $Z_i$.

The weighting matrix for a neural network is usually derived through a training process by feed the neural network with a large amount of test data. After training, the trained neural network can be put to work, where the neural network can predict the outcome for an input data (i.e. regression). However, training may also be performed on-the-fly so that there is no distinction between the training phase and the regression phase.

There are enormous literatures and references in the field related to CNN's topology, architecture, and training process. Therefore, the details of CNN techniques are not repeated here. In the present invention, the captured images from GI tract are provided to a CNN to perform diagnosis or assessment tasks.

In one embodiment, the CNN is used to detect the area of substance blocking the view in an image. In one embodiment, the CNN also detects the portion of images with subpar quality such as bad exposure (e.g., over-exposure or under-exposure) and/or motion-smear, and calculates the areas as part of the specific target area. In one embodiment, the output of CNN corresponds to a box or a polygon surrounding a specific target object. In this case, the area of this bounding box is used as an approximation of the area of the specific target object. Since the bounding box always includes some space not belonging to the specific target object, the area of the bounding box requires to be adjusted by a correction factor to obtain a better approximation of the area of the specific target object. Large box and small box may have different correction factors since a large rectangular box may have less proportion of empty space then a small box.

Since bad images may affect proper operation of the CNN, it is desirable to identify such bad images and exclude them from the objective assessment process. In one embodiment, bad images are identified and are excluded from the step of deriving the objective assessment score, where the bad images comprise over-exposed images and/or under exposed images and/or motion-smeared images and/or images not recognized by AI, but belonging to the part of the anatomy of interest.

The present invention for assessment of bowel preparation condition can be readily extended to diagnosis of certain GI tract diseases or other conditions by properly defining the specific target objects. There are diseases, such as Crohn disease, where its endoscope score has been very subjective and suffers from very large inter-observer and intra-observer variances. Therefore, the objective assessment mentioned above can be used for assessing the Crohn disease condition to provide an objective score for the disease state. As in the bowel cleanness assessment case, this will save a doctor tremendous amount of time by using this method for an objective assessment of disease state for clinical prognosis and management. Crohn disease is a chronic transmural inflammatory bowel disease that usually affects the distal ileum and colon but may occur in any part of the gastrointestinal tract. In a traditional approach, an endoscopist/doctor will examine the colonoscopy images to look for specific image characteristics of the Crohn disease, which may include inflamed areas or ulcers that may occur in patches. Inflammation in the lining of the colon may look red and swollen and ulcers may look like rows or tracts. There can be diseased tissue and healthy tissue alternating in different areas of the colon. According to one embodiment of the present invention, the diseased areas can be detected using image processing, computer vision or AI (e.g., decision tree, random forest, SVM (Support Vector Machine), CNN, etc.) techniques by defining the specific target object as the diseased areas. An objective assessment score can be derived based on the areas of the diseased areas and larger areas of the specific target objects imply higher probability or more serious state of Crohn disease.

For the Crohn disease assessment, the specific target objects can also be specified as regions free from or substantially free any features (e.g., inflamed areas or ulcers) indicative of Crohn disease. In this case, smaller areas of the specific target objects imply higher probability or more serious state of Crohn disease.

In one embodiment, objective assessment scores are derived for individual images. The objective assessment score for the overall images is then derived from the objective assessment scores. The individual assessment score for each image is derived based on the areas of the specific target objects in one individual image and the image size of one individual image.

Since sometimes the capsule stays in a region longer than the other or an endoscopist spends more time in one region than the other, the region where the capsule or the endoscope stays longer will have more images. A tract intended for examination can be divided into one or more sections, where the intended examination can be a portion of the GI tract. The images associated with the tract intended for examination are divided into corresponding groups. In one embodiment, the contribution from each section is normalized by the number of images in the respective group. For example, if the capsule or endoscope stays in the cecum for too long and take too many images, we might scale down the contribution from this section by a factor. In another embodiment, each sectional score is derived based on a subset of images in each corresponding group.

Furthermore, it has been shown that the CNN is capable of detecting the corresponding GI locations of the captured images as reported in an article by Chen et al. ("Automated and real-time validation of gastroesophageal varices under esophagogastroduodenoscopy using a deep convolutional neural network: a multicenter retrospective study (with video)", GASTROINTESTINAL ENDOSCOPY Volume 93, No. 2: 2021, pp. 424-432.e3). In one embodiment of the present invention, the GI tract location associated with the captured images is determined using image processing, computer vision or AI techniques. The derived GI tract location is then used to normalize the region contributions from the corresponding images. Furthermore, in another embodiment of the present invention, global motion estimation is used to derive the travelled distance in the GI tract and the travelled distance is used to decide the normalization factor based on the distanced travelled (e.g., the number of images per centimeter). The distance information can further enhance the accuracy of the distance travelled by global motion estimation.

In a large hollow organ like the stomach, the distance between an object from the camera may vary substantially. A same object may appear to be rather large in the captured image when the camera is very close to the object. On the other hand, the object may appear to be very small in the captured image when the object is far away from the camera. Accordingly, in another embodiment, the object distance information is used to adjust or scale the areas of specific target objects respectively, and the scaled areas of specific target objects are used for deriving the objective score. In yet another embodiment, the objective assessment score is derived from a ratio of a first sum of the areas of said one or more specific target objects in the substantial number of images from said one or more images and a second sum of entire areas of the substantial number of images from said one or more images. The first sum of the areas is scaled according to object distances of said one or more specific target objects and the second sum of entire areas is scaled by distance information within the substantial number of images respectively.

For GI images, the objects often correspond to some features on the mucosa of the GI tract, such as polyp, erosion or ulcer. In this case, the object distance corresponds to the distance between the camera of the endoscope and the object. For the case of assessing bowel preparation cleanness, the object may correspond to a debris that may be floating in the body liquid and away from the mucosa. In one embodiment of the present invention, the distance information of object is derived as from the camera of the endoscope to the mucosa in the neighborhood area of the mucosa area for which the view is blocked by the said debris. However, even for an object on the mucosa, the object may correspond a very bulging surface on the mucosa. For example, the object may be Crohn inflammation causing swelling that is bulging substantially. In this case, the distance information of object is derived as from the camera of the endoscope to the mucosa in the neighborhood area of the object. Furthermore, a weighing might be applied. In a large hollow organ like stomach, the score of a part or all of the organ is normalized by the area of anatomy of interest. In one embodiment, the object areas can be determined with object distance information. In another embodiment, the area of the image area is determined with distance information. In another embodiment the object areas and/or the area of the anatomy of interest are decided with respective distance information after the images are stitched.

The process to derive the areas of specific target objects may require a large amount of computational resources. In order to reduce the computational burden, in one embodiment of the present invention, some captured images are skipped or excluded from deriving the areas of specific target objects. For example, every other frames can be skipped. In another embodiment, a portion of one image and another portion of another image are used to derive the areas of specific target objects in order to reduce calculations. For example, the upper half image is used for odd-numbered images and lower half for even-numbered images are used to derive the areas of specific target objects.

In one embodiment, parts of images with improper imaging conditions such as over exposure, under exposure or other imaging conditions such as motion smear due to fast camera motion, are detected and excluded from calculating the areas of specific target objects. For disease score, the improper image conditions may also include bad bowel preparation areas. Images with improper imaging conditions may cause failure of the CNN-based assessment. Therefore, by excluding such images, the reliability of the CNN assessment is greatly improved. In one embodiment, an image can be excluded from score assessment due to unacceptable or improper imaging conditions within the image exceeding some threshold.

In another embodiment, the specific target objects can be classified into different categories and different weightings are assigned to different categories for calculating the overall areas of the specific target objects. For example, a very dark object can be assigned a larger weighting factor than a slightly opaque object (e.g. a bubble) in calculating the weighted sum of areas of the specific target objects for assessment of the bowel cleanness. In another example, an area with more serious disease condition (e.g. Crohn erosion or ulcer) may be assigned a larger weighting than an area with a lesser disease condition, such as erosion. In other words, seriousness/severity of a target disease is used to determine the weighting.

In one embodiment, different weightings are assigned to different specific target areas bounded by individual boxes as described above. The objective score is derived as the sum of the areas×respective weightings or areas of the bounding boxes×respective weightings.

In one embodiment, a range of the bowel is divided into multiple sections and each section has an associated score derived from the images of the corresponding section. The overall score may be a combination of scores from all sections of interest.

In one embodiment, the object distance information is used to aid categorizing the target objects (e.g., swollen or tumor) since the object distance information is useful to detect contour of different heights.

In one embodiment, the areas of the specific target objects are scaled by respective object distance and optical property of the imaging system. A method and apparatus to estimate physical area of an object using object distance and optical property of the imaging system are disclosed in U.S. Pat. No. 10,346,978 issued on Jul. 9, 2019. In another embodiment, the area of the entire image is estimated by taking into account of the distance information.

In one embodiment, each image is assigned a grade and the number of images or the percentage of images with certain grades or a ranges of grades are used for the final objective assessment. The grade may be indicative of the condition of the specific target object. For example, 10,000 images are taken in from the colon of a patient. the disease severity or bowel cleanness of this patient associated with each image can be assigned a grade between 0 and 10, with 0 as normal and 10 as the most severe condition. A final object assessment may be assigned as "Severe" if over 1000 images with grades between 7 and 10. A final object assessment may be assigned as "Moderate" if over 1000 images with grades above 5, but less than 7. A final object assessment may be assigned as "Minor" if over 500 images with grades above 3 but less than 5. A final object assessment may be assigned as "Fair" if over 500 images with grades above 2, but less or equal to 3. A final object assessment may be assigned as "Normal" if less than 10 images with grades above 2, but all other images with grades under 3.

In one embodiment, the image stitching is used to generate stitched images and the diagnosis or assessment can be done before or after the bowel images are stitched. In this case, a score can be determined as the ratio of the disease area to the total bowel lumen surface of the stitched images.

In one embodiment, for the case of diagnosis or assessment of disease, the image scores from the lumen can be combined with scores derived from other data such as X-ray, MRI, blood tests, etc. to make the final score.

In one embodiment, the objective assessment score is determined based on the grades of a subset of images to decide the overall scores. For example, 10,000 images are captured from a patient's GI tract. Among the 10,000 images, a subset consisting of 5,000 images are used to determine the objective assessment score. The 5,000 images may correspond to every other images in the original set. In another embodiment, the 5,000 images may correspond to the evenly spaced images according to travelled distance in the GI tract.

In one embodiment, the GI tract is divided into multiple sections, where each section may have a different number of images. The number of images per section or per length (i.e., travelling distance) can be used to normalize the assessment contribution from respective section. The boundary of the section can be recognized by doctors or by using image processing or AI techniques. Sometimes, the capsule goes backward (i.e., retrograde). However, the corresponding GI tract locations of the images can be recognized by doctors or using AI techniques an image by image basis.

The method mentioned above can be implemented using various programmable devices such as micro-controller, central processing unit (CPU), graphics processing unit (GPU), field programmable gate array (FPGA), digital signal processor (DSP), ASIC (Application Specific Integrated Circuit) or any programmable processor or circuitry.

Figure 4:
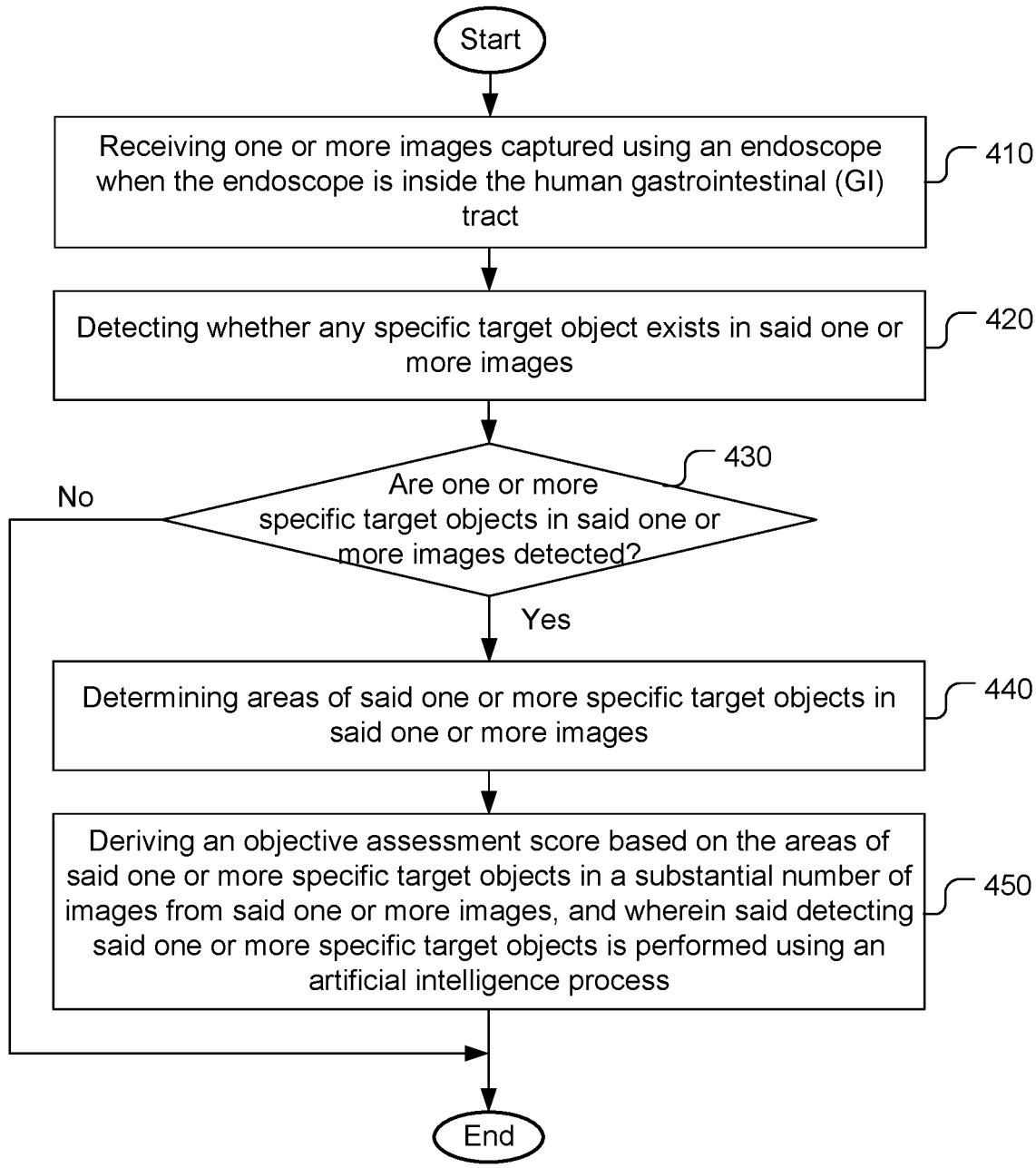
FIG. 4 illustrates an exemplary flowchart for spreading method to derive an objective assessment score according to an embodiment of the present invention.

FIG. 4 illustrates an exemplary flowchart for a method to derive an objective assessment score according to an embodiment of the present invention. According to the method, one or more images captured using an endoscope when the endoscope is inside the human gastrointestinal (GI) tract are received in step 410. Detecting whether any specific target object exists in said one or more images in step 420. Determining if one or more specific target objects in said one or more images are detected in step 430. If one or more specific target objects in said one or more images (i.e., the "Yes" path from step 430), steps 440 and 450 are performed. Otherwise (i.e., the "No" path from step 430), steps 440 and 450 are skipped. In step 440, areas of the specific target objects in the images are determined. In step 450, an objective assessment score is derived based on the areas of the specific target objects in a substantial number of images from said one or more images, wherein said detecting said one or more specific target objects is performed using an artificial intelligence process.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of objective assessment of images captured from a human gastrointestinal (GI) tract, the method comprising:
   receiving one or more images captured using an endoscope when the endoscope is inside the human gastrointestinal (GI) tract;
   detecting whether any specific target object is in said one or more images; and
   when one or more specific target objects in said one or more images are detected:
      determining area sizes of said one or more specific target objects in said one or more images;
      deriving an objective assessment score based on the area sizes of said one or more specific target objects in said one or more images;
      wherein said detecting said one or more specific target objects is performed using an artificial intelligence process; and
      wherein a travelled distance by the endoscope in the human GI tract is used to decide a normalization factor on the area sizes or a sum of the area sizes of said one or more specific target objects in said one or more images.

2. The method of claim 1, wherein individual scores for individual images in said one or more images are determined respectively, and wherein each individual score is determined based on the area sizes of said one or more specific target objects in one individual image and image size of one individual image, and when there is no specific target object detected in one individual image, the area sizes of said one or more specific target objects in one individual image are treated as zero.

3. The method of claim 2, wherein the objective assessment score is derived based on the individual scores.

4. The method of claim 1, wherein the objective assessment score is related to a sum of the area sizes of said one or more specific target objects in said one or more images.

5. The method of claim 4, wherein a number of said one or more images is used to decide a normalization factor for the sum of the area sizes of said one or more specific target objects.

6. The method of claim 1, wherein the objective assessment score corresponds to a sum of adjusted area sizes, by respective object distances of said one or more specific target objects in said one or more images.

7. The method of claim 1, wherein the objective assessment score corresponds to a weighted sum of the area sizes of said one or more specific target objects in said one or more images.

8. The method of claim 7, wherein weighting factors for the weighted sum of the area sizes of said one or more specific target objects are dependent on conditions, characteristics or seriousness/severity of said one or more specific target objects.

9. The method of claim 1, wherein the artificial intelligence process corresponds to a convolution neural network (CNN) process.

10. The method of claim 1, wherein said one or more specific target objects comprise opaque debris and turbid fluid, and the objective assessment score is indicative of bowel preparation condition.

11. The method of claim 1, wherein said one or more specific target objects comprise inflamed organ tissues, erosion or ulcers in distal ileum and colon, and the objective assessment score is indicative of Crohn disease condition.

12. The method of claim 1, wherein at least a portion of the human gastrointestinal (GI) tract intended for examination is divided into one or more sections and the images associated with said at least a portion of the human gastrointestinal (GI) tract are divided into corresponding groups, and wherein sectional scores are derived for corresponding sections and each sectional score is derived based on a sum of area sizes of said one or more specific target objects in the images in each respective group normalized by a number of images in each respective group, and the objective assessment score is derived from the sectional scores.

13. The method of claim 12, wherein each sectional score is derived based on a subset of images in each corresponding group.

14. The method of claim 1, wherein bad images are identified and are excluded from said deriving the objective assessment score, and wherein the bad images comprise over-exposed images and/or under exposed images and/or motion-smeared images.

15. The method of claim 1, wherein object distances of said one or more specific target objects are used to aid identifying said one or more specific target objects.

16. The method of claim 1, wherein said one or more images are stitched to form one or more stitched images, and wherein said detecting said one or more specific target objects, said determining the area sizes of said one or more specific target objects and said deriving the objective assessment score are performed based on said one or more stitched images.

17. The method of claim 1, wherein said detecting said one or more specific target objects, said determining the area sizes of said one or more specific target objects and said deriving the objective assessment score are performed based on a subset of said one or more images.

18. The method of claim 1, wherein individual images of said one or more images are assigned grades according to the area sizes of said one or more specific target objects and the grades are indicative of disease severity or bowel cleanness, and wherein a number of images or a percentage of images with certain grades or a ranges of grades are used to determine the objective assessment score.

19. A method of objective assessment of images captured from a human gastrointestinal (GI) tract, the method comprising:
receiving one or more images captured using an endoscope when the endoscope is inside the human gastrointestinal (GI) tract;
detecting whether any specific target object is in said one or more images; and
when one or more specific target objects in said one or more images are detected:
determining area sizes of said one or more specific target objects in said one or more images;
deriving an objective assessment score based on the area sizes of said one or more specific target objects in said one or more images;
wherein said detecting said one or more specific target objects is performed using an artificial intelligence process; and
wherein the area sizes of said one or more specific target objects in said one or more images are scaled according to respective object distances of said one or more specific target objects respectively in said one or more images, and wherein scaled area sizes of said one or more specific target objects in said one or more images are used for said deriving the objective assessment score; and
wherein the objective assessment score is derived from a ratio of a first sum of the area sizes of said one or more specific target objects, scaled according to the respective object distances of said one or more specific target objects in said one or more images and a second sum of entire area sizes of said one or more images scaled by distance information within said one or more images respectively.

20. The method of claim 19, wherein individual scores for individual images in said one or more images are determined respectively, and wherein each individual score is determined based on the area sizes of said one or more specific target objects in one individual image and image size of one individual image, and when there is no specific target object detected in one individual image, the area sizes of said one or more specific target objects in one individual image are treated as zero.

21. The method of claim 20, wherein the objective assessment score is derived based on the individual scores.

22. The method of claim 19, wherein bad images are identified and are excluded from said deriving the objective assessment score, and wherein the bad images comprise over-exposed images and/or under exposed images and/or motion-smeared images.

23. A method of objective assessment of images captured from a human gastrointestinal (GI) tract, the method comprising:
receiving one or more images captured using an endoscope when the endoscope is inside the human gastrointestinal (GI) tract;
detecting whether any specific target object is in said one or more images; and
when one or more specific target objects in said one or more images are detected:
determining area sizes of said one or more specific target objects in said one or more images;
deriving an objective assessment score based on the area sizes of said one or more specific target objects in said one or more images;

wherein said detecting said one or more specific target objects is performed using an artificial intelligence process; and wherein the area sizes of said one or more specific target objects in said one or more images are scaled according to respective object distances of said one or more specific target objects respectively in said one or more images, and wherein scaled area sizes of said one or more specific target objects in said one or more images are used for said deriving the objective assessment score; and wherein when one specific target object is away from a mucosa of the human gastrointestinal (GI) tract, the respective object distance of said one specific target object is derived from a first distance from a camera of the endoscope to the mucosa of the human gastrointestinal (GI) tract in a neighborhood area associated with said one specific target object.

24. The method of claim 23, wherein individual scores for individual images in said one or more images are determined respectively, and wherein each individual score is determined based on the area sizes of said one or more specific target objects in one individual image and image size of one individual image, and when there is no specific target object detected in one individual image, the area sizes of said one or more specific target objects in one individual image are treated as zero.

25. The method of claim 24, wherein the objective assessment score is derived based on the individual scores.

26. The method of claim 23, wherein bad images are identified and are excluded from said deriving the objective assessment score, and wherein the bad images comprise over-exposed images and/or under exposed images and/or motion-smeared images.

* * * * *